United States Patent [19]

Gutbier

[11] Patent Number: 4,529,116
[45] Date of Patent: Jul. 16, 1985

[54] METHODS OF AND DEVICES FOR DETERMINING THE SOLDERING CAPABILITY OF A SOLDER WAVE

[75] Inventor: Ernst A. Gutbier, North Andover, Mass.

[73] Assignee: AT&T Technologies, Inc., Berkeley Heights, N.J.

[21] Appl. No.: 489,677

[22] Filed: Apr. 28, 1983

[51] Int. Cl.³ ............................................. G01N 13/00
[52] U.S. Cl. ...................................... 228/103; 73/64.4; 73/432 R; 228/56.5; 228/180.1
[58] Field of Search ...................... 228/180 R, 37, 260, 228/103, 56.5; 428/210; 73/64.4, 432 Z

[56] References Cited

U.S. PATENT DOCUMENTS

| | | | |
|---|---|---|---|
| 1,804,508 | 5/1931 | Nicholson | 428/210 |
| 2,993,815 | 7/1961 | Treptow | 428/210 |
| 3,118,788 | 1/1964 | Hensler | 428/210 |
| 3,732,792 | 5/1973 | Tarnopol et al. | 428/210 |
| 3,857,290 | 12/1974 | Aitken et al. | 73/432 Z |
| 4,180,199 | 12/1979 | O'Rourke et al. | 228/102 |
| 4,227,415 | 10/1980 | Spirig | 73/432 Z |
| 4,467,638 | 8/1984 | Greenstein | 228/103 |

FOREIGN PATENT DOCUMENTS 1330558 9/1973 United Kingdom .............. 73/432 Z

Primary Examiner—Kenneth J. Ramsey
Assistant Examiner—Kurt Rowan

[57] ABSTRACT

First and second transparent metallized gauge plates (52 and 52') of solder-nonwettable, heat-resistant material, such as glass or quartz, each have a solder wave test pattern in the form of spaced parallel metal strips (56 and 56') formed thereon. The metal strips (56) on the first gauge plate (52) are of progressively increasing widths, with a narrowest strip located adjacent one edge of the plate and a widest strip located adjacent an opposite edge of the plate. The metal strips 56' on the second gauge plate (52') are of uniform widths. The first gauge plate (52) is engaged with a solder wave (34) to measure the activation level of a soldering flux (44) being introduced into the solder wave, and thereby to determine the capability of the solder wave to produce properly soldered printed circuit board assemblies (10). The second gauge plate is engaged with the solder wave (34) to measure and/or adjust other flow characteristics of the solder wave, such as a width of solder wave impingement (80) on the printed circuit board assemblies (10).

18 Claims, 9 Drawing Figures

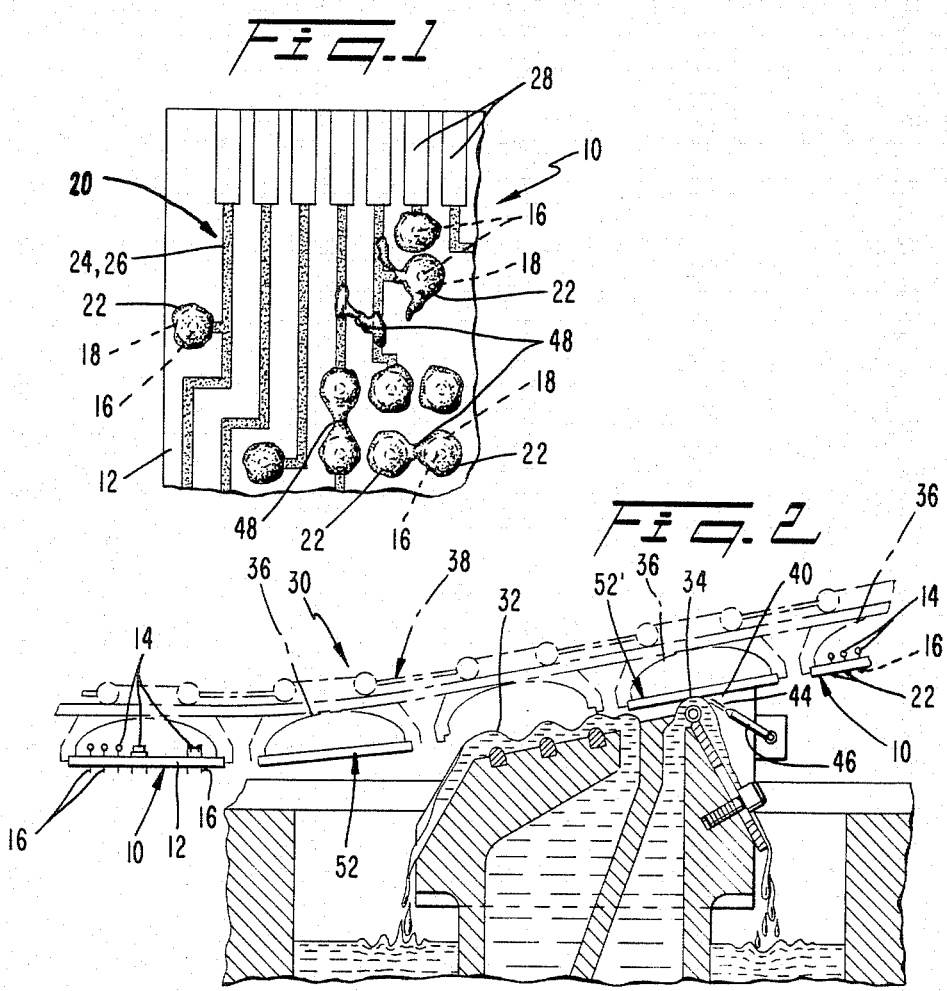
Fig. 1
Fig. 2
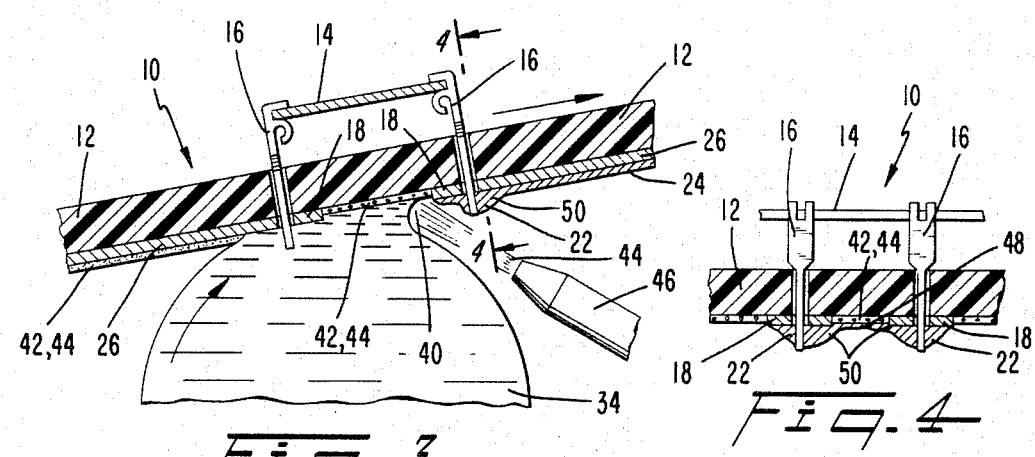
Fig. 3
Fig. 4

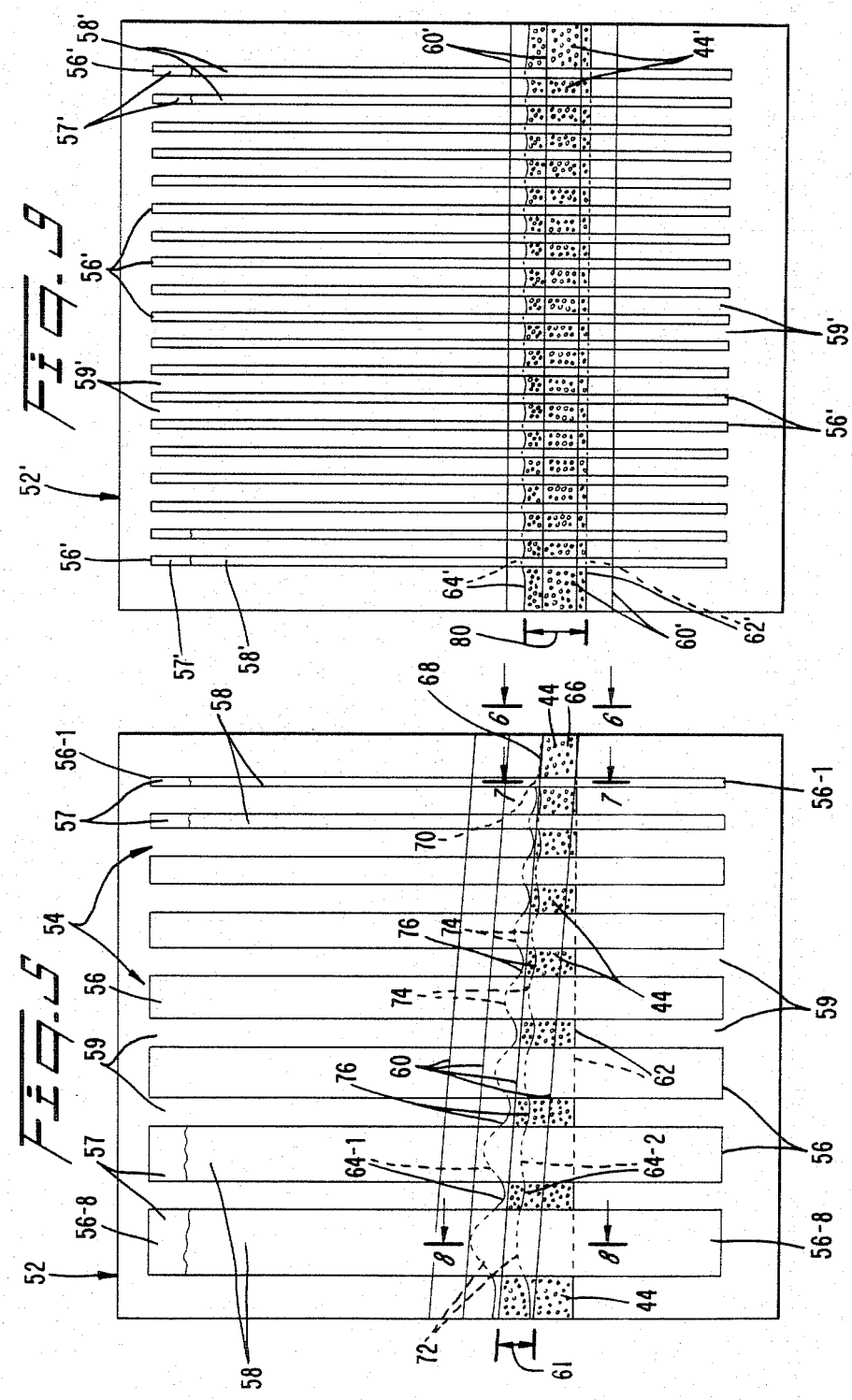

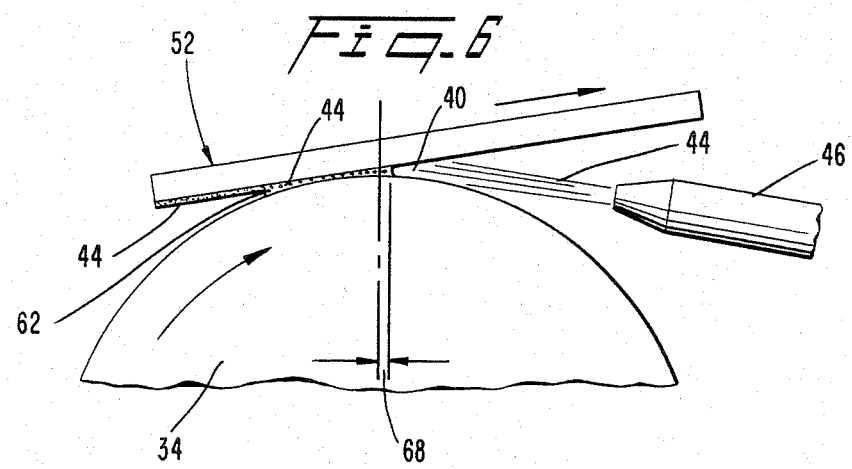
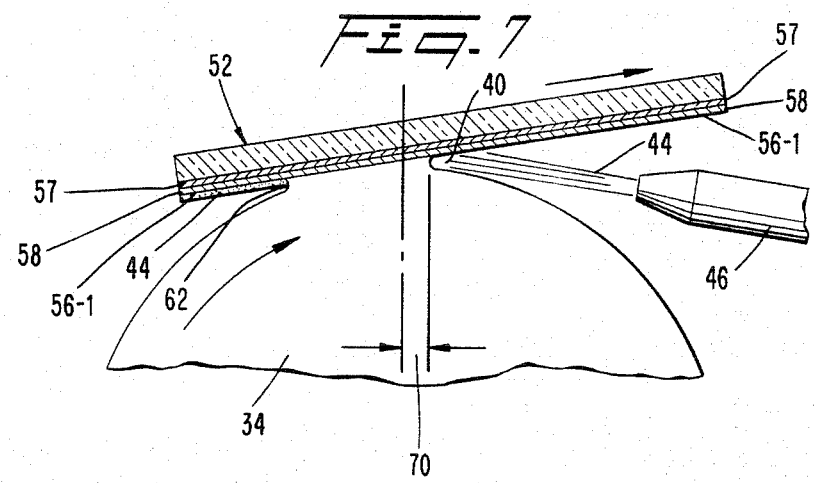
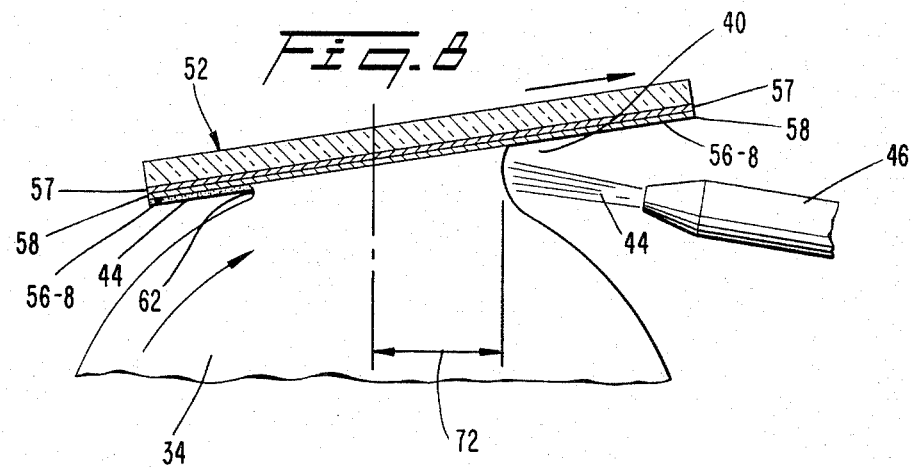

METHODS OF AND DEVICES FOR DETERMINING THE SOLDERING CAPABILITY OF A SOLDER WAVE

TECHNICAL FIELD

This invention relates to methods of and devices for determining the soldering capability of a solder wave, and more particularly to the determining of the soldering capability of a solder wave utilizing transparent solder wave gauge plates having metal test patterns formed on the plates.

BACKGROUND OF THE INVENTION

In the manufacture of a printed circuit board assembly, a plurality of electrical components are mounted on a printed circuit board by extending leads of the components through apertures in the board from one side of the board. Projecting portions of selected ones of the leads on an opposite side of the board then are crimped over to retain the components on the board, with the remaining leads projecting from the opposite side of the board. The leads then are soldered to contact pads surrounding the apertures, and protective solder coatings are formed on conductor paths of the board, by passing the board assembly over a molten solder wave, such as the dual solder wave disclosed in the U.S. Pat. No. 4,101,066, issued July 18, 1978, to V. A. Corsaro and E. A. Gutbier.

As is known in the art, a molten solder surface tends to oxidize even when traveling in a molten solder wave, and thus has an inherent high surface tension. As a result, as the printed circuit board assemblies pass over the solder wave, unless a suitable fluxing agent is employed, the molten solder in the solder wave tends not to separate between adjacent contact pads and/or conductor paths, thus producing solder defects in the form of solder crossovers or bridges (i.e., shorts) between the contact pads and/or conductor paths. This is particularly true where adjacent contact pads and/or conductor paths are close together, such as on the order of one-tenth of an inch or less. This producing of solder defects is further aggravated where only selected leads of the components are crimped as noted hereinabove, since the remaining projecting leads tend to produce "drag out" of solder as the leads exit from the solder wave. Accordingly, it is standard practice to apply a suitable soldering flux to the printed circuit board assemblies prior to their passage over the molten solder wave, and/or to spray a soldering flux into the point at which the printed circuit board assemblies exit from the wave, which is known in the art as a "peel back" region. The degree to which a particular soldering flux then reduces solder crosses in the soldering operation is dependent upon the activation level of the flux, that is, the ability of the flux to reduce oxidation and surface tension formation in the solder wave in the "peel back" region.

In the past, the activation level of different fluxes and their soldering performance, and thus the capability of a solder wave to produce properly soldered printed circuit board assemblies when one of the fluxes is used in a soldering operation, has been determined by conducting extensive soldering quality yield studies. This is disadvantageous because of the time and expense involved, and because the studies do not provide for periodic "on site" indications of the capability of a particular solder wave, with which a selected flux is being used, to produce properly soldered printed circuit board assemblies under variable process conditions.

Another known procedure for determining the capability of a solder wave to produce properly soldered printed circuit board assemblies involves the engaging of a transparent gauge plate with the solder wave in the same manner that the printed circuit board assemblies engage the solder wave in a soldering operation, and then observing the physical behavior characteristics of the solder wave as the wave impinges on the transparent plate. This procedure, however, produces unreliable results because the behavior of the molten solder wave as the wave impinges on the solder-nonwettable surface of the transparent gauge plate does not correspond to the solder wave impinging on solder-wettable metal surfaces, such as the conductor paths of a printed circuit board assembly.

Accordingly, a purpose of this invention is to provide a new and improved procedure for making an "on-site" determination of the capability of a solder wave to solder printed circuit board assemblies with a minimum number of solder defects, by emulating more closely the physical behavior characteristics of the molten solder wave in an actual soldering operation.

SUMMARY OF THE INVENTION

Briefly, the capability of a solder wave to produce properly soldered parts is determined by engaging a solder-nonwettable surface on one side of a transparent member, and at least one solder-wettable surface portion formed on the solder-nonwettable surface, with the solder wave. By observation through the transparent member from a second opposite side of the transparent member, a flow characteristic of the flowing solder in the solder wave which engages the solder-wettable surface portion then is compared with a value of the flow characteristic known to produce properly soldered parts. For example, the degree to which the flowing solder in the solder wave adheres to the solder-wettable surface portion may be compared with a predetermined degree of adherence known to produce properly soldered parts.

More specifically, the transparent member has a plurality of spaced parallel solder-wettable strips formed on one side of the member. In use, the one side of the transparent member and portions of the solder-wettable strips are engaged with the solder wave such that the engaged strip portions extend parallel to the direction of flow of the solder wave. In one embodiment of the invention, the solder-wettable strips may be arranged in progressively increasing widths, with a narrowest one of the strips located adjacent one edge of the transparent member and a widest one of the strips located adjacent an opposite edge of the transparent member. The transparent member also may include at least one inclined gauge line which extends across the different width solder-wettable strips, and which is representative of a predetermined degree of adherence known to produce properly soldered parts. In another embodiment of the invention, the solder-wettable strips may be of uniform widths with at least one gauge line extending perpendicularly across the strips. The latter embodiment of the invention, by way of example, initially can be utilized to adjust a behavior characteristic of the solder wave, such as the degree of impingement of the solder wave, to a desired value for a soldering operation. The first embodiment of the invention then can be utilized to determine the activation level of a soldering flux being introduced into the solder wave.

BRIEF DESCRIPTION OF THE DRAWING

FIG. 1 is a partial plan view of a printed circuit side of a printed circuit board assembly illustrating a solder crossover or bridging condition;

FIG. 2 is a partial elevational view of a wave soldering apparatus in which the invention may be utilized;

FIG. 3 is an enlarged view of a portion of the wave soldering apparatus shown in FIG. 2 during a soldering operation;

FIG. 4 is a cross-sectional view taken along the line 4—4 in FIG. 3;

FIG. 5 is a plan view of one embodiment of a transparent metallized solder wave gauge plate in accordance with the invention;

FIG. 6 is a cross-sectional view taken along the line 6—6 in FIG. 5;

FIG. 7 is a cross-sectional view taken along the line 7—7 in FIG. 5;

FIG. 8 is a cross-sectional view taken along the line 8—8 in FIG. 5; and

FIG. 9 is a plan view of another embodiment of a transparent metallized solder wave gauge plate in accordance with the invention.

DETAILED DESCRIPTION

FIGS. 1 and 2 disclose a printed circuit board assembly 10 which includes a printed circuit board 12 and a plurality of electrical components 14 (shown only in FIG. 2) having leads 16 extending through apertures in the board from one side thereof. On the opposite side of the printed circuit board 12 projecting portions of the component leads 16 are soldered to electrically conductive copper terminal pads 18 (shown only in FIG. 1) of a printed circuit 20 on the board, as for example by passing the board over molten solder in a wave soldering operation. The projecting portions of selected ones of the leads 16 are bent over in a known manner (not shown) to retain the electrical components 14 on the printed circuit board prior to and during the wave soldering operation.

With further reference to FIG. 1, as the molten solder wets the terminal pads 18 and the projecting portions of the component leads 16, and then coalesces, soldered connections 22 are formed between the leads and the terminal pads. At the same time, the solder forms protective conductive solder layers 24 on copper conductor paths 26 of the printed circuit 20, except for gold plated fingers 28 of the printed circuit, which are suitably masked during the wave soldering process.

The forming of the soldered connections 22 between the component leads 16 and the terminal pads 18, and the forming of the protective solder layers 24 on the printed circuit conductor paths 26, may be accomplished utilizing soldering apparatus of any suitable type, such as a bi-directional solder wave type apparatus 30, shown partially in FIG. 2 and disclosed in more detail in the aforementioned U.S. Pat. No. 4,101,066, the disclosure of which is hereby incorporated by reference. The bi-directional solder wave apparatus 30 includes first and second solder waves 32 and 34, respectively, through which the printed circuit board assemblies 10 are advanced in succession in carriers 36 of a suitable conveyor 38. The first solder wave 32 is of a cascade type in which solder flows counter to the direction of movement of the printed circuit board assemblies 10 and in which the printed circuit sides of the boards 12 engage a series of solder crests in succession. The second solder wave 34 is of a fountain type in which solder flows in the direction of movement of the printed circuit board assemblies 10 and in which the printed circuit boards 12 engage an upwardly flowing portion of the solder wave to form a solder "peel back" region 40 at a point at which the printed circuit board assemblies exit from the solder wave.

Prior to the printed circuit board assemblies 10 being passed over the solder waves 32 and 34 by the conveyor 38, the printed circuit sides of the boards 12 are coated with a layer 42 (partially shown in FIG. 3) of a suitable soldering flux 44 in a fluxing station (not shown) in a known manner, thus indirectly introduing the soldering flux into the solder waves when the assemblies pass over the solder waves in a soldering operation. At the same time, additional soldering flux 44 may be introduced directly into the "peel back" region 40 of the second solder wave 34 from a bank of spray nozzles 46 (only one shown) as illustrated in FIGS. 2 and 3. The soldering flux layer 42 on each of the printed circuit boards 12 reduces oxidation on the terminal pads 18 and conductor paths 26, and reduces the surface tension in the surfaces of the flowing molten solder waves 32 and 34, to facilitate the forming of the soldered connections 22 and the solder layers 24. Similarly, the soldering flux 44 introduced into the "peel back" region 40 by the spray nozzles 46 further reduces the surface tension of the adjacent surface portions of the second solder wave 34 to facilitate the soldering operation.

However, referring to FIG. 1, when the activation level of the soldering flux 44 being utilized is too low, such that the surface tension in the surface of the second solder wave 34 is not sufficiently reduced, the molten solder in the second solder wave does not readily separate between the terminal pads 18 and/or the conductor paths 26 of the printed circuit boards 12. Accordingly, the solder tends to bridge across and between the terminal pads 18 and/or conductor paths 26 to produce defects in the form of bridges or crossovers 48 (electrical shorts) in the printed circuit 20 on the printed circuit board 12.

More specifically, referring to FIGS. 3 and 4, which disclose one of the electrical components 14 passing over the second solder wave 34, the solder bridging condition is attributed, at least in part, to the soldering flux 44 which is being utilized in the soldering operation not producing sufficient fluxing action to cause separation of the solder engaged with portions of the printed circuit board 12 between the terminal pads 18 and/or the conductor paths 26. For example, specific reference is made to FIG. 4, which illustrates two closely adjacent component leads 16 and their associated terminal pads 18 just after passing over the second solder wave 34. In FIG. 4 it is seen that a small reservoir of the soldering flux layer 42 exists on the portion of the printed circuit board 12 between the two terminal pads 18, with a body 50 of solder which has wetted to the terminal pads to form associated ones of the soldered connections 22, also extending over the flux layer between the soldered connections. This condition is attributed to the soldering flux 44 having too low of an activation level to reduce the surface tension in the solder body 50 sufficiently to cause separation of the solder therein, whereby the solder body produces one of the above-mentioned solder bridges or shorts 48 between the terminal pads 18.

In accordance with this invention, referring to FIG. 5, a transparent metallized gauge plate 52 as shown in this figure can be utilized to determine the capability of the soldering apparatus 30, and in particular the second solder wave 34, to produce properly soldered printed circuit boards 12 without the formation of the solder bridges or shorts 48 between the terminal pads 18 and/or the conductor paths 26. In this connection, the transparent metallized gauge plate 52 has a test pattern 54 of solder-wettable metal formed on an underside of the plate as viewed in FIG. 5.

More specifically, the test pattern 54 includes a series of spaced parallel strips 56 each having an inner adhesive layer 57 (FIGS. 5, 7 and 8), such as tantalum, and an exterior layer 58 (FIGS. 5, 7 and 8) formed of the same metal (e.g., copper) as the conductor paths 26 on the printed circuit boards 12. The metal strips 56 are arranged on the transparent gauge plate 52 in progressively increasing widths, with a narrowest strip located at one edge of the gauge plate and a widest strip located at an opposite edge of the gauge plate. By way of illustration, a narrowest strip 56-1 can have a width of 50 mils and a widest strip 56-8 can have a width of 450 mils. The metal strips 456 can be separated by solder-nonwettable portions 59 of the transparent gauge plate 52 having a width, for example, of 200 mils.

The transparent metallized gauge plate 52 also is provided with a plurality of parallel inclined gauge lines 60 (FIG. 5) having an angle of inclination 61, such as on the order of five to six degrees, which is representative of a "peel back" condition in the second solder wave 34 which will produce properly soldered printed circuit board assemblies 10. The gauge lines 60 may be engraved or otherwise suitably formed in a top side of the gauge plate 52, as viewed in FIG. 5, so as to extend across the metal strips 56 between the opposite edges of the plate on preselected uniform spacings, such as 250 mils. While four of the gauge lines 60 are shown in FIG. 5 for purposes of illustration, more or less of the gauge lines may be provided on the gauge plate 52 as desired. In this connection, as viewed in FIG. 5, a plurality of the gauge lines 60 are advantageous from the standpoint of achieving alignment of the right-hand end of the "peel back" line of contact 64-1 or 64-2, with the right-hand end of one of the gauge lines 60 in a test operation as subsequently described herein.

The construction of the transparent metallized gauge plate 52 as above described is based in part of the principle that the degree of wetting of the solder in the solder wave 34 (FIG. 2) to one of the conductor paths 26 (FIG. 1) of one of the printed circuit boards 12 or one of the metal strips 56 (FIG. 5) on the gauge plate, and thus the magnitude of "peel back" in the solder wave in the "peel back" region 40 (FIG. 2), is essentially proportional to the width of the conductor path or the metal strip. Thus, when the transparent metallized gauge plate 52 is mounted in one of the printed circuit board carriers 35 (FIG. 2) of the conveyor 38 and brought into engagement with the solder wave 34 so that the metal strips 56 extend parallel to the direction of flow of the solder wave, an entrance line of contact 62 (FIGS. 5, 6, 7 and 8) between the solder wave and the gauge plate extends essentially horizontally across the gauge plate with portions of the line of contact between the metal strips 56 visible through the transparent portions 59 of the gauge plate from the top side of the gauge plate. At the same time, a serpentine "peel back" line of contact 64-1 or 64-2 between the solder wave 34 and the gauge plate 52 extends upward from right to left in FIG. 5, at an angle which is dependent upon the activation level of the soldering flux 44 being used in the soldering operation, with portions of the "peel back" line of contact also visible from the top side of the gauge plate between the metal strips 56.

More specifically, adjacent the right-hand side of the gauge plate 52 as viewed in FIG. 5, the solder wave 34 engages a solder nonwettable portion 66 of the plate. As a result, as is best shown in FIG. 6, the solder does not wet or adhere to the guage plate portion 66 and the degree of solder "peel back" 68 at this point is essentially zero. Rather, the solder in the solder wave 34 remains separated from the solder-nonwettable portion of the gauge plate by a previously applied layer of the solder flux 44, and by associated bubbles which form in the flux layer by engagement thereof with the molten solder.

However, referring to FIG. 7, a portion of the solder wave 34 which engages the narrowest metal strip 56-1 on the gauge plate 52 wets to the copper layer 56 of the strip so as to produce a slight "peel back" 70 of the solder portion when the gauge plate is engaged with the solder wave. In contrast, referring to FIG. 8, a large "peel back" 72 is produced in a portion of the solder wave 34 which engages the widest metal strip 56-8 as a result of the increased solder-wetting area of this strip. Similarly, a "peel back" 74 (FIG. 5) in other successive portions of the solder wave 34 engaged with the metal strips 56 between the narrowest and widest strips progressively increases from the narrowest to the widest strip as shown in FIG. 5, with the amount of "peel back" 76 in the solder portions which engage the solder-nonwettable gauge plate between the strips being reduced in magnitude. Thus, the resultant serpentine "peel back" line of contact 64-1 or 64-2 between the solder wave 34 and the gauge plate 52 is inclined upward at an angle from right to left as viewed in FIG. 5, as above described.

The construction of the transparent metallized gauge plate 52 is further based on the principle that the activation level of the soldering flux 44 is inversely proportional to the amount of "peel back" 68, 70, 72 and 74 in the "peel back" region 40 of the solder wave 34. In this connection, as the solder in the solder wave 34 is engaged by one of the printed circuit boards 12 in a soldering operation, or by the transparent metallized gauge plate 52 in a test operation, when the soldering flux 44 has a low activation level the flux will not effectively reduce the surface tension of the solder in the "peel back" region 40 of the solder wave. As a result, as the solder wets and adheres to the printed circuit board terminal pads 18 and conductor paths 26, or to the gauge plate metal strips 56, the high surface tension of the solder in the "peel back" region 40 overcomes the force of gravity such that the adhering solder travels along with the printed circuit board 12 or gauge plate 52 a substantial distance to produce a large "peel back" condition. In contrast, when the soldering flux 44 has a high activation level, the flux reduces the surface tension of the solder in the "peel back" region 40. Accordingly, as the solder wets and adheres to the terminal pads 18 and conductor paths 26, or the gauge plate metal strips 56, gravity overcomes the adherence of the solder to the terminal pads and conductor paths, or to the metal strips, to preclude any substantial travel of the solder with the printed circuit board 12 or the gauge plate 52, thereby producing a low "peel back" condition.

Thus, referring to FIG. 5, the "peel back" line of contact 64-1, which extends generally at an angle greater than the angle of inclination 61 of the gauge lines 60 and above an adjacent lower one of the gauge lines, indicates a low activation level of the soldering flux 44 in the wave soldering process which will produce improperly soldered printed circuit boards 12 having solder bridges or shorts 48. In contrast, the "peel back" line of contact 64-2, which extends generally at an angle less than the angle of inclination 61 of the gauge lines 60 and below the adjacent gauge line, indicates a high activation level of the soldering flux 44 which will produce properly soldered printed circuit boards 12 without solder bridges or shorts 48.

FIG. 9 discloses another transparent metallized gauge plate 52' in accordance with the invention, which can be utilized to adjust solder flow in the second solder wave 34 to an optimum value prior to use of the transparent metallized gauge plate 52 to determine the activation level of the soldering flux 44. The gauge plate 52' also can be utilized to determine other behavior characteristics of the second solder wave 34 which can be expected to occur in an actual soldering operation. In this connection, since the conductor paths 26 on the printed circuit boards 12 normally are of a uniform width, the gauge plate 52' also has a plurality of parallel metal strips 56' of uniform width formed on one side of the gauge plate. The metal strips 56' may be of the same width as the conductor paths 26 on the printed circuit boards 12, such as 10-20 mils. In the alternative, referring to the right-hand side of FIG. 5, it is seen that the degree to which solder in the solder wave 34 adheres to the narrower metal strips 56 does not vary substantially for strips having widths up to 200 mils (third strip from the right in FIG. 5). Accordingly, the metal strips 56' on the transparent metallized gauge plate 52' can be formed to widths up to on the order of 200 mils, if so desired.

When the transparent metallized gauge plate 52 is mounted in one of the printed circuit board carriers 36 (FIG. 2) of the conveyor 38 and engaged with the second solder wave 34, referring further to FIG. 9, an entrance line of solder wave contact 62' with the gauge plate, and a "peel back" line of solder wave contact 64' with the gauge plate, define a width of solder wave impingement 80. In this connection, the metal strips 56' on the gauge plate 52' have spacings 59' therebetween, such as 100-200 mils, which are of a width such that the width of solder wave impingement 80 is readily visible between the metal strips from above the gauge plate. A plurality of parallel gauge lines 60' (four shown) having preselected uniform spacings, such as 250 mils, are formed in a top side of the gauge plate 52' and extend across the gauge plate perpendicularly to the metal strips 56' between opposite edges of the gauge plate. As in the case of the transparent metallized gauge plate 52, the metal strips 56' of the gauge plate 52' include inner adhesive layers 57' (tantalum) and exterior layers 58' of the same metal (copper) as the conductor paths 26 on the printed circuit boards.

Each of the transparent metallized gauge plates 52 and 52' can be formed of any suitable heat-resistant material which can be exposed to a soldering temperature (e.g., 500° F.) for a preselected time period, such as two to three minutes, without damage thereto. For example, the gauge plates 52 and 52' can be formed from tempered glass such as that available from the Corning Glass Works of Corning, New York under the tradename "PYREX". The gauge plates 52 or 52' also can be formed from heat-resistant quartz.

The metal strips 56 and 56' can be formed on the transparent gauge plates 52 and 52', respectively, utilizing known metallization techniques. For example, a tantalum adhesive layer (not shown) can be formed on the gauge plate 52 or 52' by sputtering. A copper layer (not shown) then can be formed on the tantalum layer by electroless plating or evaporation. The metal strips 56 or 56' then are produced on the gauge plate 52 or 52', respectively, by known photolithographic and etching steps.

Referring to FIG. 2, in making an "on site" determination of the soldering capability of the second solder wave 34 in a soldering operation, the transparent metallized gauge plates 52 and 52' may be mounted in respective ones of the printed circuit board carriers 36 of the conveyor 38 with the second gauge plate 52' in a leading one of the carriers. The conveyor 38 then is energized to pass the gauge plates 52 and 52' over the abovementioned fluxing station (not shown), to form a layer of the soldering flux 44 (FIGS. 3–5) on the gauge plate 52 and a corresponding layer of flux (FIG. 9) on the gauge plate 52'. The conveyor 30 then moves the transparent metallized gauge plate 52' over the first solder wave 32 and into engagement with the second solder wave 34 as shown in FIG. 2, whereupon the conveyor is temporarily de-energized.

Solder flow in the second solder wave 34 then can be adjusted in a known manner to produce an optimum value of the width of wave impingement 80 (FIG. 9), utilizing the gauge lines 60' (FIG. 9) on the transparent metallized gauge plate 52' as a reference. At the same time, other behavior characteristics of the solder wave 34, such as uniformity of wave impingement, and uniformity and degree of wetting of the solder wave to the metal strips 56' in the gauge plate 52', can be observed to determine the capability of the solder wave to produce properly soldered printed circuit board assemblies 10. The gauge plate 52' also can be utilized to help insure that the gauge plate 52 will subsequently be properly oriented horizontally upon being engaged with the solder wave 34, by determining that proper horizontal orientation exists between the gauge plate 52' and the "peel back" line of contact 64' of the solder wave 34.

The conveyor 38 then can be re-energized to move the transparent metallized gauge plate 52 over the first solder wave 32 and into engagement with the second solder wave 34, whereupon the conveyor again is de-energized. In this connection, as viewed in FIG. 5, the gauge plate 52 preferably is engaged with the second solder wave 34 such that a right-hand end portion of the "peel back" line of contact 64-1 or 64-2 is located on or closely adjacent the right-hand end of one of the gauge lines 60. The remainder of the "peel back" line of contact 64-1 or 64-2 with respect to the gauge line 60 then is observed as above-described, to determine the capability of the solder wave 34 to produce properly soldered printed circuit boards 12.

While in the disclosed embodiments of the invention the second solder wave 34 flows parallel to and in the direction of movement of the printed circuit board assemblies 10, it also is considered to be within the purview of the invention to utilize transparent metallized gauge plates similar to the gauge plates 52 and 52' to evaluate other types of solder waves. For example, the transparent metallized gauge plates 52 and 52', or modifications thereof, also could be utilized to evaluate the characteristics of the first solder wave 32, if so desired.

In summary, new and improved devices in the form of the transparent metallized solder wave gauge plates 52 and 52', and a method of using the gauge plates to determine the capability of a solder wave, such as the second solder wave 34, to form properly soldered parts, such as the printed circuit board assemblies 10, have been disclosed. In this connection, by way of example, the transparent metallized gauge plate 52' (FIG. 9) can be utilized to compare the width of impingement 80 of the solder wave 34 to an optimum value, and to adjust the height and flow of the solder wave to achieve the optimum value. The gauge plate 52' also can be utilized to determine various other characteristics of the solder wave 34, including relative orientation between the gauge plate and the solder wave, in preparation for evaluation of the activation level of the soldering flux 44 (FIGS. 2 and 3) by the transparent metallized gauge plate 52 (FIG. 5).

The gauge plate 52 then can be utilized to determine the activation level of the soldering flux 44 by being engaged with the second solder wave 34 such that a right-hand end portion of the "peel back" line of contact 64-1 or 64-2 between the solder wave and the gauge plate, as viewed in FIG. 5, is located on or closely adjacent the right-hand end of one of the gauge lines 60 as shown in FIG. 5. The "peel back" of the solder wave 34, as represented by one of the "peel back" lines of contact 64-1 or 64-2, then is compared to the gauge line 60, which represents a flux activation level capable of producing properly soldered printed circuit board assemblies 10. In this regard the upper "peel back" line of contact 64-1 indicates a low soldering flux activation level such that the solder wave 34 is not capable of producing properly soldered printed circuit board assemblies 10 without solder bridges or shorts 48 (FIGS. 1 and 4). In contrast, the lower "peel back" line of contact 64-2 indicates a high soldering flux activation level such that the solder wave 34 is capable of producing properly soldered printed circuit board assemblies 10.

What is claimed is:

1. A method of determining the capability of a solder wave to produce properly soldered parts when the parts are passed over the solder wave in a soldering operation, which comprises the steps of:
    positioning adjacent to the solder wave, a transparent member having at least one solder-wettable surface portion formed on a solder-unwettable surface on one side of the transparent member;
    engaging the solder-unwettable surface of the transparent member and the solder-wettable surface portion with the solder wave; and
    comparing by observation through the transparent member from a second opposite side of the transparent member, at least one flow characteristic of the flowing solder in the solder wave which engages the solder-wettable surface portion of the transparent member, with a value of the flow characteristic which produces properly soldered parts.

2. The method as recited in claim 1, in which:
    the flow characteristic which is compared is the degree to which the flowing solder in the solder wave adheres to the solder-wettable surface portion of the transparent member.

3. The method as recited in claim 1, in which the solder-wettable surface portion on the transparent member is an elongated strip, and in which:
    the elongated strip is engaged with the solder wave such that the strip extends parallel to a direction of flow of the solder wave.

4. The method as recited in claim 1, in which the solder-wettable surface portion on the transparent member is an elongated strip, and in which:
    soldering flux is introduced into the solder wave to reduce surface tension and oxidation in the solder wave; and
    the elongated strip is engaged with an upwardly flowing portion of the solder wave.

5. The method as recited in claim 1, in which:
    portions of a plurality of spaced parallel strips of solder-wettable material on the solder-wettable surface of the transparent member are engaged with the solder wave such that the engaged strip portions extend parallel to the direction of the flow of the solder wave.

6. The method as recited in claim 5, in which:
    the spaced parallel strips of solder-wettable material have progressively increasing widths, with a narrowest one of the strips located adjacent one edge of the transparent member and a widest one of the strips located adjacent an opposite edge of the transparent member.

7. The method as recited in 5, in which:
    the strips of solder-wettable material have uniform widths.

8. The method as recited in claim 7, in which:
    the degree to which the solder wave impinges on the transparent member is compared with and adjusted to a value which produces properly soldered parts;
    a second transparent member then is engaged with the solder wave, the second transparent member having spaced parallel strips of solder-wettable material formed on a solder-nonwettable surface on one side of the transparent member, with a narrowest one of the strips located adjacent one edge of the transparent member and a widest one of the strips located adjacent an opposite edge of the transparent member; and
    the degree to which the flowing solder in the solder wave adheres to the solder-wettable strips on the second transparent member then is compared with a predetermined degree of adherence which produces properly soldered parts.

9. A solder wave measuring device, which comprises:
    a transparent member having first and second opposite sides and formed of a solder-nonwettable material which is resistant to damage from temporary engagement with molten solder;
    a plurality of strips of solder-wettable material formed on the first side of the transparent member so as to be visible from the second side of the transparent member; and
    a gauge line formed on one of the sides of the transparent member and extending substantially across all of said member and also extending transversely across all of the strips of solder-wettable material, the gauge line being representative of a flow characteristic of a solder wave which will produce proper soldering of a part which is passed over the solder wave.

10. The solder wave measuring device as recited in claim 9, in which the transparent member is formed of glass.

11. The solder wave measuring device as recited in claim 9, in which the transparent member is formed of quartz.

12. The solder wave measuring device as recited in claim 9, in which:
    each strip of solder-wettable material has an exterior surface formed of copper.

13. The solder wave measuring device as recited in claim 9, wherein the strips of solder-wettable material are spaced strips running parallel to one another.

14. The solder wave measuring device as recited in claim 13, in which:
    the spaced parallel strips of solder-wettable material are of different widths.

15. The solder wave measuring device as recited in claim 14, in which:
    the spaced parallel strips of solder-wettable material are arranged on the first side of the transparent member in progressively increasing widths, with a narrowest one of the metal strips located adjacent a first edge of the transparent member and a widest one of the metal strips located adjacent a second opposite edge of the transparent member.

16. The solder wave measuring device as recited in claim 15, wherein the gauge line extends at an inclined angle across the spaced parallel strips of solder-wettable material, the gauge line being representative of a degree of adherence of a solder wave to the solder-wettable strips which will produce proper soldering of a part which is passed over the solder wave.

17. The solder wave measuring device as recited in claim 13, in which:
    the spaced parallel strips of solder-wettable material are of uniform widths.

18. The solder wave measuring device as recited in claim 17, which further comprises:
    a second gauge line formed on one of the sides of the transparent member, both gauge lines extending perpendicularly across the uniform width strips of solder-wettable material.

* * * * *